United States Patent
Chewter et al.

(10) Patent No.: US 6,939,995 B2
(45) Date of Patent: Sep. 6, 2005

(54) PROCESS FOR THE PREPARATION OF ISOPROPANOL

(75) Inventors: Leslie Andrew Chewter, Amsterdam (NL); Wilhelmus Cornelis Nicolaas Dekker, Amsterdam (NL); Stephane Jean Pierre Lecrivain, Amsterdam (NL); Carolus Matthias Anna Maria Mesters, Amsterdam (NL); Andrew Neave Rogers, Amsterdam (NL); Lydia Singoredjo, Amsterdam (NL)

(73) Assignee: Shell Oil Company, Houston, TX (US)

( * ) Notice: Subject to any disclaimer, the term of this patent is extended or adjusted under 35 U.S.C. 154(b) by 172 days.

(21) Appl. No.: 10/294,192

(22) Filed: Nov. 14, 2002

(65) Prior Publication Data

US 2003/0149314 A1 Aug. 7, 2003

(30) Foreign Application Priority Data

Nov. 16, 2001 (EP) .............................. 01309673

(51) Int. Cl.⁷ .............................................. C07C 37/08
(52) U.S. Cl. ....................................... 568/798; 568/881
(58) Field of Search ................................. 568/798, 881

(56) References Cited

U.S. PATENT DOCUMENTS

| | | | |
|---|---|---|---|
| 2,456,187 A | 12/1948 | Guinot ....................... | 260/690 |
| 3,932,534 A | 1/1976 | Fukunaga et al. ...... | 260/618 H |
| 5,015,786 A | 5/1991 | Araki et al. ................. | 568/798 |
| 5,017,729 A * | 5/1991 | Fukuhara et al. ........... | 568/798 |
| 5,160,497 A | 11/1992 | Juguin et al. ............... | 568/798 |
| 2003/0153793 A1 * | 8/2003 | Sakuth et al. ............... | 568/798 |
| 2004/0034256 A1 * | 2/2004 | Fallon et al. ............... | 568/804 |

FOREIGN PATENT DOCUMENTS

| | | | | |
|---|---|---|---|---|
| EP | 0434485 A1 | | 11/1990 | ........... C07C/37/08 |
| WO | WO 200162692 A1 * | | 8/2001 | ........... C07B/61/00 |

OTHER PUBLICATIONS

E. de Ruiter and J. C. Jungers, Bull. Soc. Chim. Belg., 58, p. 230, 1949, no translation.

R.Z.C. van Meerten, A.H.G.M. Beaumont, P.F.M.T. van Nisselrooij and J.W.E. Coenen, Surface Science 135 (1983), pp. 565–579.

* cited by examiner

Primary Examiner—Michael L. Shippen

(57) ABSTRACT

Process for the preparation of isopropanol is provided, wherein a benzene-containing feed of acetone is hydrogenated to obtain isopropanol and hydrogenation products of benzene.

Combination of such a process with a process for the preparation of phenol and combination of such a process with a series of separation steps is provided.

24 Claims, 1 Drawing Sheet

PROCESS FOR THE PREPARATION OF ISOPROPANOL

FIELD OF THE INVENTION

The present invention relates to a process for the hydrogenation of acetone to prepare isopropanol.

BACKGROUND OF THE INVENTION

Isopropanol is a very useful intermediate in organic synthesis as well as a commercially important solvent.

Acetone is produced in large amounts as a by-product in the manufacture of phenol by the cumene process. In a cumene process benzene is alkylated with propene and/or isopropanol to synthesize cumene, cumene is oxidized into cumene hydroperoxide and cumene hydroperoxide is acid cleaved to generate phenol and acetone. The acetone produced by this cumene-process contains benzene. As indicated in for example EP-A-0434485, the production of acetone in the cumene process is considered a disadvantage because the demand for phenol increases much faster than the demand for acetone. Therefore it is suggested in EP-A-0434485 to hydrogenate acetone, obtained in the cumene process into isopropanol, and recycle the isopropanol into the cumene process.

EP-A-0434485 does not describe the presence of benzene in the acetone generated by the cumene process.

The hydrogenation of benzene is much more difficult than the hydrogenation of acetone. This is illustrated, for example, by an article by E. de Ruiter and J. C. Jungers, Bull. Soc. Chim. Belg., 58 page 230, 1949, where it is stated that when a mixture of acetone and benzene is hydrogenated the acetone reacts first.

Recently it has become desirable to convert acetone, obtained in the cumene process, into isopropanol which can be used for other purposes than the recycle into the cumene process. The presence of any amounts of benzene, however, makes it disadvantageous to use the isopropanol for any purpose other than recycling to the cumene process.

The removal of traces of benzene from acetone by distillation is very difficult. Removal of benzene from isopropanol after hydrogenation is even more difficult because of the close boiling points of benzene and isopropanol.

SUMMARY OF THE INVENTION

Accordingly, a process for the preparation of isopropanol is provided comprising hydrogenating an acetone feed comprising acetone and benzene thereby producing isopropanol and hydrogenation products of benzene.

Further provided is a process for the preparation of phenol comprising:
a) alkylating benzene with isopropanol and/or propylene thereby producing cumene;
b) oxidizing the cumene of step a) thereby producing cumene hydroperoxide;
c) cleaving the cumene hydroperoxide by acid thereby producing phenol and benzene-containing acetone;
d) optionally concentrating the benzene-containing acetone produced in step c); and
e) hydrogenating the benzene-containing acetone of step c) or, if present, step d) thereby producing isopropanol containing hydrogenation products of benzene.

Also provided is a process for the hydrogenation of a benzene-containing feed of acetone containing comprising the steps of:

i) hydrogenating a benzene-containing feed of acetone in the presence of hydrogen thereby producing a reaction product containing isopropanol;
ii) separating gaseous products from the reaction product of i) thereby producing a liquid reaction product;
iii) separating light by-products and unreacted acetone from the liquid reaction product of ii) thereby producing a crude isopropanol product;
iv) separating heavy by-products from the crude isopropanol product of iii) thereby producing a purified isopropanol product; and
v) recycling unreacted acetone and/or part of the light by-products obtained in step iii) and/or part of the heavy by-products in step iv) to the hydrogenation step i).

DETAILED DESCRIPTION OF THE INVENTION

Figure 1:
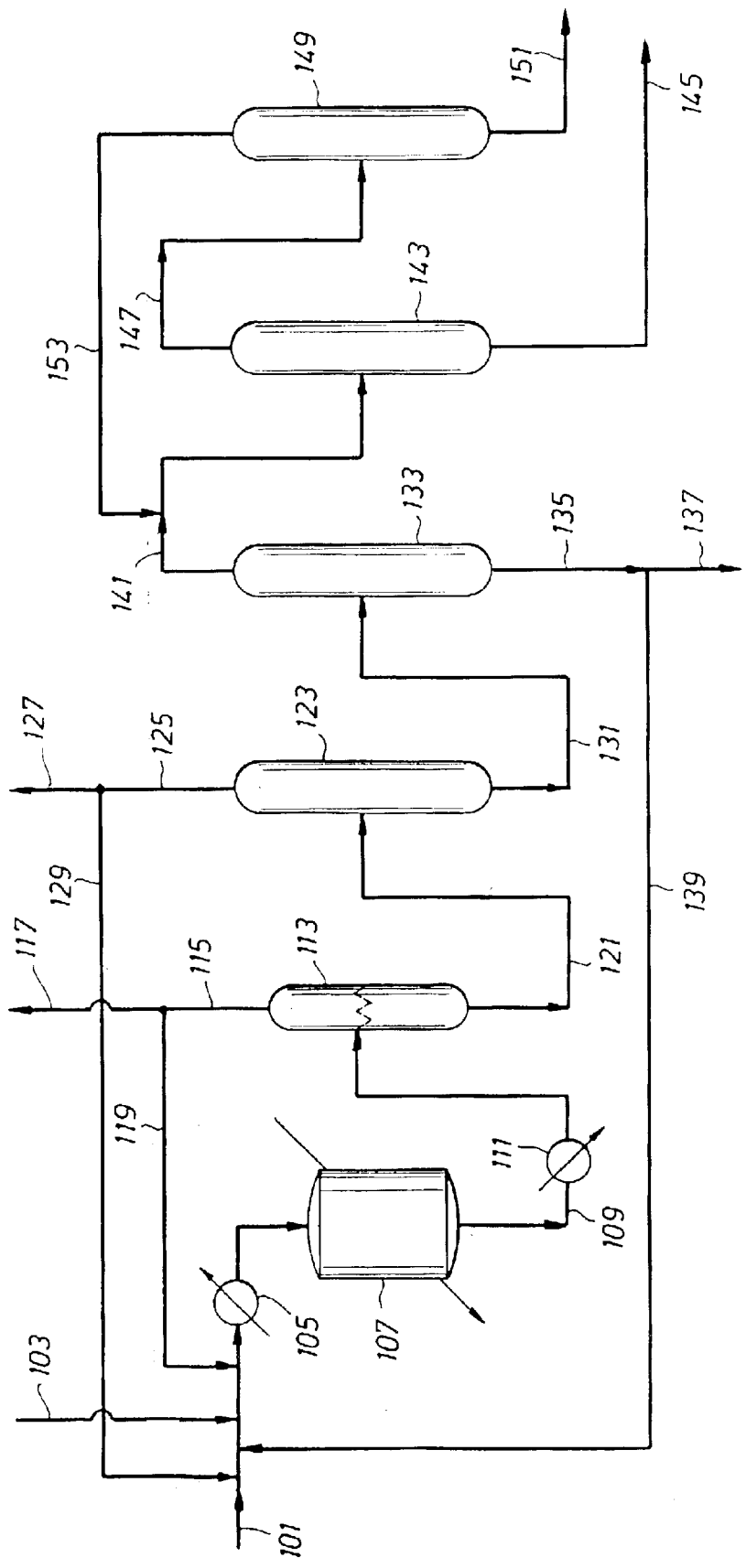
FIG. 1 represents a schematic flow diagram of an embodiment of the invention.

A process is provided wherein benzene-containing acetone, such as acetone generated by the cumene process, can be converted in an economically attractive manner to isopropanol useful for other purposes than recycling. Such an economically attractive process has been found by hydrogenating benzene present in the acetone feed. In a process as described by EP-A-0434485, it is advantageous to hydrogenate acetone only.

A process for the preparation of isopropanol is provided, wherein a benzene-containing feed of acetone is hydrogenated to obtain isopropanol and hydrogenation products of benzene.

The process according to the invention can advantageously be used to prepare isopropanol containing a reduced amount of benzene or even essentially no benzene, which is suitable for various applications.

By isopropanol containing essentially no benzene is understood isopropanol that contains less than 2 ppm (2 mg/kg), suitably less than 1 ppm (1 mg/kg), preferably less than 0.4 ppm (0.4 mg/kg), more preferably less than 0.1 ppm ($0.1 \times 10^{-6}$), even more preferably less than 20 ppb (20 $\mu$g/kg), and most preferably no benzene.

In the process according to the invention benzene can, for example, be hydrogenated into cyclohexane, cyclohexene or cyclohexadiene.

Preferably more than 70%, more preferably more than 90%, even more preferably more than 95% and most preferably 99% to 100% of the benzene is hydrogenated.

Preferred factors to influence the hydrogenation of benzene include the type and amount of catalyst used; the temperature; the quantity of each of the reactants or the flow-rate at which each of the reactants are fed to the reactor. Preferably hydrogenation of benzene is accomplished by using a specific type of catalyst, capable of hydrogenating benzene, hydrogenation catalyst, whereas all other factors are preferably chosen such to obtain an optimal hydrogenation.

Hydrogenation of acetone and benzene in the benzene-containing acetone feed can be carried out in one or more separate steps but is preferably carried out simultaneously. Therefore the catalyst is preferably a catalyst, capable of hydrogenating acetone and benzene simultaneously.

Preferably the hydrogenation of acetone and benzene is carried out in the presence of a catalyst containing a metal capable of hydrogenation.

Preferred metals for hydrogenation include copper, nickel, platinum, palladium, ruthenium, and rhodium. One metal or a combination of metals can be used. Preferably the metal is supported on a carrier. Suitable carriers include, for example, carbon, alumina, silica, zirconia and titania supports. Silica supports are preferred because the use of a silica support results in a very high selectivity with regard to the hydrogenation of acetone into isopropanol. Preferred examples of silica supports include Kieselguhr, precipitated silica and silica gel.

An especially preferred catalyst is a hydrogenation catalyst comprising nickel, preferably supported on a carrier. A catalyst comprising nickel on a silica carrier is most preferred.

For practical reasons, currently, metals may be present in amounts within the range from 5% w/w to 80% w/w metal on a carrier. If the hydrogenation metal is nickel, catalysts containing more than 25% w/w nickel, preferably more than 50% w/w nickel and more preferably in the range of 50 up to 70% w/w nickel, are preferred.

A preferred way to achieve simultaneous hydrogenation of acetone and benzene is the use of a nickel catalyst having a dispersion and nickel content such that the nickel surface is at least 15 $m^2$ nickel per gram catalyst. More preferably the nickel surface is at least 20 $m^2$ nickel per gram catalyst, and most preferably the nickel surface is at least 30 $m^2$ nickel per gram catalyst. A suitable practical upper limit is formed by 50 $m^2$ nickel per gram catalyst.

The nickel surface can be determined by measurement of the monolayer capacity for chemisorption of hydrogen as described by J. W. E Coenen and B. C. Linsen, in "Physical and Chemical Aspects of Adsorbents and Catalysts" B. C. Linsen, ed. Academic Press (1970) 471 or R. Z. C. van Meerten, A. H. G. M. Beaumont, P. F. M. T. van Nisselrooij and J. W. E. Coenen, Surface Si. 135(1983) 565. For the determination of the nickel surface, the monolayer is defined as the amount of hydrogen adsorbed at 1 bar pressure of hydrogen and 293 K. The adsorption of hydrogen was determined after reduction at 725 K for 4 hours, subsequent evacuation during 2 hours at 675 K, and controlled hydrogen admission.

The catalyst has preferably a bulk density in the range from 800–1200 kg/$m^3$, preferably a BET-surface area in the range of 100–250 $m^2$/g, preferably a pore volume in the range of 0.20 to 0.50 $cm^3$/g and preferably an extrudate diameter in the range from 1 to 6 mm.

Preferably the catalyst is present as a fixed bed. In an advantageous embodiment the process according to the invention is operated at trickle flow. That is, liquid acetone trickles along the surface of the catalyst, which is packed in an atmosphere full of hydrogen gas.

Preferably the molar ratio of hydrogen to acetone should be at least 1. More preferably the molar ratio of hydrogen to acetone lies in the range from 1:1 to 10:1, most preferably in the range from 1.5:1 to 5:1.

The hydrogenation process can be performed at a wide range of reaction temperatures, reaction pressures, superficial liquid and gas velocities used. Dependent on the type of catalyst used, each of those reaction conditions is optimized such as to obtain optimal hydrogenation of the benzene. For example, a less active catalyst will require a higher reaction temperature. Furthermore the use of higher superficial liquid and gas velocities requires higher temperatures, whereas the use of a lower reaction temperature can require lower superficial liquid and gas velocities. Preferably temperatures applied in the reactor lie in the range from 40 to 150° C. more preferably in the range from 60 to 130° C. As the catalyst ages, higher temperatures may be required. Reaction pressure preferably lies in the range from 1 to 100 barg, more preferably in the range from 10 to 40 barg. A higher pressure will result in increased costs for compressing the gas whereas a lower pressure can result in poor conversion rates.

The superficial gas velocity is preferably in the range of 0.01–10 m/s, and the superficial liquid velocity is preferably in the range of 0.0001–0.1 m/s.

The gas is preferably essentially pure hydrogen, though this hydrogen can contain minor amounts, for example in the range of 0 to 15% w/w, of for example methane, ethane, nitrogen and other impurities.

The process according to the invention can advantageously be applied to feeds of acetone containing benzene in a wide range of concentrations. Possible benzene concentrations in a feed of acetone could lie in the range from 0.01 ppm to 1% benzene, and more likely in the range from 0.1 ppm to 100 ppm benzene. The process according to the invention is further especially advantageous for feeds of acetone containing at least 0.5 ppm benzene, and its advantages become more pronounced as the benzene concentration increases to at least 1 ppm. The advantages are most pronounced for acetone feeds containing at least 1.5 ppm benzene.

The process according to the invention can very advantageously be combined with a process for the preparation of phenol. The present invention therefore also provides a process for the preparation of phenol comprising:

a) alkylating benzene with isopropanol and/or propylene to synthesize cumene;
b) oxidizing the cumene of step (a) into cumene hydroperoxide;
c) acid cleaving the cumene hydroperoxide generating phenol and benzene-containing acetone;
d) preferably concentrating the benzene contaminated acetone, generated in step c); and
e) hydrogenating the benzene-containing acetone of step d) into isopropanol containing hydrogenation products of benzene.

Steps a) to c) can conveniently be carried out as described in for example U.S. Pat. Nos. 5,015,786 and 5,160,497 which disclosures are herein incorporated by reference. Step d) can conveniently be carried out by distillation. Step e) is preferably carried out as described herein before. Isopropanol generated in step e) can be used as a solvent in various applications. If desired isopropanol generated in step e) can also be recycled to step a). Such a recycle can conveniently be carried out as described in for example U.S. Pat. Nos. 5,015,786 and 5,160,497 which disclosures are herein incorporated by reference.

To further improve the quality of the isopropanol the process according to the invention is preferably combined with a series of separation steps.

The invention therefore also provides a process for the hydrogenation of a benzene-containing feed of acetone as described herein before comprising the steps of:

i) hydrogenation of a benzene-containing feed of acetone in the presence of hydrogen, yielding a reaction product containing isopropanol;
ii) separation of gaseous products from the reaction product of i); yielding a liquid reaction product;

iii) separation of light by-products and unreacted acetone from the liquid reaction product of ii), yielding a crude isopropanol product;

iv) separation of heavy by-products from the crude isopropanol product of iii), yielding a purified isopropanol product; and v) recycling unreacted acetone and/or part of the light by-products obtained in step iii) and/or part of the heavy by-products in step iv) to the hydrogenation in step i).

Such a process comprising a train of separation steps results in a very high quality of isopropanol. Furthermore the recycling of the by-products as listed in step v) improves the selectivity of the process.

The process can be carried out batch-wise, semi batch-wise or continuously. Suitably, the process is performed in a continuous manner. In such a continuous process a, preferably preheated, preferably pre-mixed, feed of benzene-contaminated acetone and hydrogen is fed to step i) for start-up. Subsequently the acetone and benzene are, preferably simultaneously, hydrogenated. The effluent of step i) can contain isopropanol, by-products such as di-isopropylether and/or hexyleneglycol, optionally hydrogenation products of benzene, such as for example cyclohexane, and, if any, unreacted hydrogen and/or acetone.

In step ii) a subsequent separation of gaseous products from the reaction product in step i) is carried out. Preferably a gas-liquid separator is used for this purpose. The gaseous products can comprise amongst others vapourized by-products and unreacted hydrogen. Preferably part of the gaseous product is purged and the remainder is preferably recycled to step i). Step ii) yields a liquid reaction product. Subsequently light by-products and unreacted acetone are separated from this liquid reaction product in step iii). Preferably this separation is accomplished by distillation. This separation yields a crude isopropanol product from which the heavy by-products are separated in step iv). This separation is also preferably accomplished by distillation. The separation yields a purified isopropanol product. In a preferred embodiment this purified isopropanol product is even further processed to yield a finalized isopropanol product. Preferably such a further processing into finalized isopropanol product is carried out by additional steps of:

vi) separation of an azeotrope of isopropanol, water and cyclohexane from the purified isopropanol obtained in step iv) yielding a finalized isopropanol product;

vii) separation of the azeotrope of isopropanol, water and cyclohexane obtained in step vi) in water and an azeotrope of isopropanol and cyclohexane; and viii) optionally recycling the azeotrope of isopropanol and cyclohexane obtained in step vii) to step vi).

The separations in step vi) and vii) are preferably carried out by distillation.

Unreacted acetone and part of the light by-products obtained in step iii) and part of the heavy by-products in step iv) are recycled to the hydrogenation in step i). In a preferred embodiment the recycle stream from step iii) to step i) comprises mainly acetone and di-isopropyl ether. Preferably the recycle stream from step iv) to step i) comprises mainly hexylene glycol. By recycling these by-products the selectivity of the process is improved resulting in an improved overall yield of isopropanol.

An illustration of a process according to the invention is now described by reference to FIG. 1.

A feed of benzene-containing acetone (101) is mixed with a feed of fresh hydrogen (103), preheated in a heat exchanger (105) and fed into a reactor (107), containing a 55–62% w/w nickel on silica catalyst, having a nickel surface of 34 m$^2$/g, in a fixed catalyst bed. A stream of reaction effluent (109) is withdrawn from the reactor (107) and cooled in a heat exchanger (111). After cooling, the gaseous compounds in the reaction effluent are separated from the liquid compounds in a gas-liquid separator (113). At the top of the gas-liquid separator (113) a stream of gas (115) is withdrawn. Part of this stream (115) is purged (117), whereas the other part is recycled to the reactor (119). At the bottom of the gas-liquid separator a stream of liquid (121) is withdrawn and fed into a distillation column (123). At the top of this distillation column (123) a stream of light products (125) is withdrawn. The stream (125) comprises mainly unreacted acetone and the by-product di-isopropyl ether. Part of this stream of light products (125) is purged (127), whereas the other part is recycled to the reactor (129). At the bottom of this distillation column (123) a stream of crude isopropanol (131) is withdrawn and fed into a second distillation column (133). At the bottom of this second distillation column (133) a stream of heavy products (135) is withdrawn. The stream (135) comprises mainly the by-product hexylene glycol. Part of this stream of heavy products (135) is purged (137), whereas the other part is recycled to the reactor (139). At the top of this second distillation column (133) a stream of purified isopropanol (141) is withdrawn and fed into a third distillation column (143). From the bottom of this third distillation column (143) a stream of finalized isopropanol is obtained (145). From the top of this third distillation column (143) a stream of azeotrope of cyclohexane, water and isopropanol (147) is obtained which is fed into a fourth distillation column (149). From the bottom of this fourth distillation column (149) a stream of water is obtained (151), which is discarded. From the top of the fourth distillation column (149) a stream of azeotrope of cyclohexane and isopropanol (153) is obtained that is recycled to the third distillation column (143).

The invention is further illustrated by the following non-limiting examples.

EXAMPLES

A reactor tube having a length of 35 cm, an internal diameter of 10 mm was provided with a fixed bed containing 5 grams of a catalyst as specified in table 1. An acetone feed containing 50 ppm (50 mg/kg) benzene was fed to the reactor at a weight hourly space volume (WHSV) as indicated in table 1. The acetone feed was hydrogenated in the presence of hydrogen and a catalyst and under a pressure and temperature as stated in table 1. The benzene conversion and acetone conversion are given in table 1. The selectivity towards isopropanol, based on total conversion products of acetone was >99%. Benzene content of the effluent isopropanol product was determined by gas-chromatography/mass spectrometry at a single ion mode mass 78. The benzene content of the effluent isopropanol is given in table 1.

| Example | Catalyst | T (° C.) | P (barg) | mol H₂/mol acetone | WHSV (kg feed/kg cat/hr) | Acetone conv. (% w/w) | Benzene conv. (% w/w) | Benzene left in end product |
|---|---|---|---|---|---|---|---|---|
| 1 | Leuna 6564 tl 1.2 | 90 | 20 | 2 | 1.5 | >99.9 | >99.9 | <20 ppb |
| 2 | Leuna 6512 AS | 130 | 20 | 2 | 1.5 | 99.9 | >99.9 | <20 ppb |
| 3 | Leuna 6512 AS | 70 | 20 | 2 | 0.5 | >99.9 | >99.9 | 26 ppb |
| 4 | Leuna 6512 AS | 90 | 20 | 2 | 0.5 | >99.9 | >99.9 | <20 ppb |
| 5 | Leuna 6512 AS | 110 | 20 | 2 | 0.5 | >99.9 | >99.9 | <20 ppb |

Leuna 6512 AS is a 55-62 % w/w nickel on silica catalyst, having a nickel surface of 34 m$^2$/gram catalyst, a bulk density of 850–1150 kg/m$^3$, a BET surface are of 180-240 m$^2$/gram catalyst and a Pore volume of 025–045 cm$^3$/gram catalyst (Leuna-Catalyst 6512 AS obtained from CRI KataLeuna).
Leuna 6564 tl 1.2 is a 28 % w/w nickel on alumina catalyst, having a nickel surface of 43 m$^2$/gram catalyst, a bulk density of 810–910 kg/m$^3$, a BET surface are of 100–120 m$^2$/gram catalyst and a Pore volume of 0.38–0.46 cm$^3$/gram catalyst (Leuna-Catalyst 6564 tl 1.2 obtained from CRI KataLeuna).

We claim:

1. A process for the preparation of isopropanol comprising hydrogenating an acetone feed comprising acetone and benzene thereby producing isopropanol and hydrogenation products of benzene, wherein the hydrogenation is carried out in the presence of a nickel catalyst comprising more than 25 wt % nickel and having a nickel surface of at least 15 m$^2$ nickel per gram catalyst.

2. The process of claim 1 wherein the catalyst is present as a fixed bed.

3. The process of claim 1 wherein the process is operated at trickle flow.

4. The process of claim 2 wherein the process is operated at trickle flow.

5. The process of claim 1 wherein the feed of acetone comprises up to 1% benzene.

6. The process of claim 2 wherein the feed of acetone comprises up to 1% benzene.

7. The process of claim 3 wherein the feed of acetone comprises up to 1% benzene.

8. A process for the preparation of phenol comprising:
   a) alkylating benzene with isopropanol and/or propylene thereby producing cumene;
   b) oxidizing the cumene of step a) thereby producing cumene hydroperoxide;
   c) cleaving the cumene hydroperoxide by acid thereby producing phenol and benzene-containing acetone;
   d) optionally concentrating the benzene-containing acetone produced in step c); and
   e) hydrogenating the benzene-containing acetone of step c) or, if present, step d) thereby producing isopropanol containing hydrogenation products of benzene, wherein the hydrogenation is carried out in the presence of a nickel catalyst comprising more than 25 wt % nickel and having a nickel surface of at least 15 m$^2$ nickel per gram catalyst.

9. The process of claim 8 wherein the catalyst is present as a fixed bed.

10. The process of claim 8 wherein step e) is operated at trickle flow.

11. The process of claim 9 wherein step e) is operated at trickle flow.

12. The process of claim 8 wherein step d) is present.

13. A process for the hydrogenation of a benzene-containing feed of acetone comprising the steps of:
   i) hydrogenating a benzene-containing feed of acetone in the presence of hydrogen thereby producing a reaction product containing isopropanol, wherein the hydrogenation is carried out in the presence of a nickel catalyst comprising more than 25 wt % nickel and having a nickel surface of at least 15 m$^2$ nickel per gram catalyst;
   ii) separating gaseous products from the reaction product of i) thereby producing a liquid reaction product;
   iii) separating light by-products and unreacted acetone from the liquid reaction product of ii) thereby producing a crude isopropanol product;
   iv) separating heavy by-products from the crude isopropanol product of iii) thereby producing a purified isopropanol product; and
   v) recycling unreacted acetone and/or part of the light by-products obtained in step iii) and/or part of the heavy by-products in step iv) to the hydrogenation step i).

14. The process of claim 13 wherein the catalyst is present as fixed bed.

15. The process of claim 13 wherein step i) is operated at trickle flow.

16. The process of claim 14 wherein step i) is operated at trickle flow.

17. A process for the hydrogenation of a benzene-containing feed of acetone comprising the steps of:
   i) hydrogenating a benzene-containing feed of acetone in the presence of hydrogen thereby producing a reaction product containing isopropanol;
   ii) separating gaseous products from the reaction product of i) thereby producing a liquid reaction product;
   iii) separating light by-products and unreacted acetone from the liquid reaction product of ii) thereby producing a crude isopropanol product;
   iv) separating heavy by-products from the crude isopropanol product of iii) thereby producing a purified isopropanol product;
   v) recycling unreacted acetone and/or part of the light by-products obtained in step iii) and/or part of the heavy by-products in step iv) to the hydrogenation step i);
   vi) separating an azeotrope of isopropanol, water and cyclohexane from the purified isopropanol produced in step iv) thereby producing a finalized isopropanol product;
   vii) separating the azeotrope of isopropanol, water and cyclohexane produced in step vi) in water and an azeotrope of isopropanol and cyclohexane; and
   viii) optionally recycling the azeotrope of isopropanol and cyclohexane produced in step vii) to step vi).

18. The process of claim 17 wherein the hydrogenation is carried out in the presence of a nickel catalyst comprising more than 25 wt % nickel and having a nickel surface of at least 15 m² nickel per gram catalyst.

19. The process of claim 18 wherein the catalyst is present as a fixed bed.

20. The process of claim 18 wherein the process is operated at trickle flow.

21. The process of claim 18 wherein the feed of acetone comprises up to 1% benzene.

22. The process of claim 17 wherein the catalyst is present as a fixed bed.

23. The process of claim 17 wherein the process is operated at trickle flow.

24. The process of claim 17 wherein the feed of acetone comprises up to 1% benzene.

* * * * *